United States Patent
Busch et al.

(10) Patent No.: US 8,351,671 B2
(45) Date of Patent: Jan. 8, 2013

(54) MOTION CORRECTION IN NUCLEAR IMAGING

(75) Inventors: Marc Busch, Cologne (DE); Ralph Brinks, Hagen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 412 days.

(21) Appl. No.: 12/670,272

(22) PCT Filed: Jul. 11, 2008

(86) PCT No.: PCT/IB2008/052811
§ 371 (c)(1), (2), (4) Date: Jan. 22, 2010

(87) PCT Pub. No.: WO2009/013661
PCT Pub. Date: Jan. 29, 2009

(65) Prior Publication Data
US 2010/0202664 A1    Aug. 12, 2010

Related U.S. Application Data

(60) Provisional application No. 60/951,968, filed on Jul. 26, 2007.

(51) Int. Cl.
*G06K 9/00* (2006.01)
*A61B 6/00* (2006.01)

(52) U.S. Cl. ......................................... 382/131; 378/21
(58) Field of Classification Search .......... 382/128–134, 382/275, 107; 378/4, 21, 69; 700/29; 600/407, 600/427, 436, 426; 250/363.04
See application file for complete search history.

(56) References Cited

U.S. PATENT DOCUMENTS

| | | | | |
|---|---|---|---|---|
| 5,210,421 A * | 5/1993 | Gullberg et al. | ......... | 250/363.04 |
| 6,310,968 B1 * | 10/2001 | Hawkins et al. | ............... | 382/131 |
| 6,947,585 B1 | 9/2005 | Jones | | |
| 6,980,683 B2 | 12/2005 | Jones | | |
| 7,603,165 B2 * | 10/2009 | Townsend et al. | ............ | 600/427 |
| 7,813,783 B2 * | 10/2010 | Thomas et al. | ............... | 600/407 |
| 8,027,715 B2 * | 9/2011 | Sayeh | ........................... | 600/426 |
| 2005/0123183 A1 | 6/2005 | Schleyer et al. | | |
| 2006/0140482 A1 | 6/2006 | Koehler | | |
| 2006/0235295 A1 | 10/2006 | Boese et al. | | |

FOREIGN PATENT DOCUMENTS

WO   2007015199 A2   2/2007

OTHER PUBLICATIONS

Klein, et al., Fine-Scale Motion Detection Using Intrinsic List Mode PET Information, Proceedings of the IEEE Workshop on Mathematical Methods in Biomedical Image Analysis (MMBIA '01), 2001, pp. 71-78, IEEE Computer Society, Washington, DC.
Lu et al., Tomographic Motion Detection and Correction Directly in Sinogram Space, Physics in Medicine and Biology, Apr. 2002, pp. 1267-1284, vol. 47, issue 8, abstract attached.

(Continued)

*Primary Examiner* — Kanjibhai Patel

(57) ABSTRACT

A radiation detection apparatus (100) acquires projection data of an object that is subject to motion during the acquisition. The apparatus includes a motion modeler (142) and a motion compensator (142) that cooperate to compensate for a motion of the object during the acquisition. In one example, the projection data includes list mode positron emission tomography data and the apparatus compensates for cardiac motion.

24 Claims, 6 Drawing Sheets

OTHER PUBLICATIONS

Figure 1:
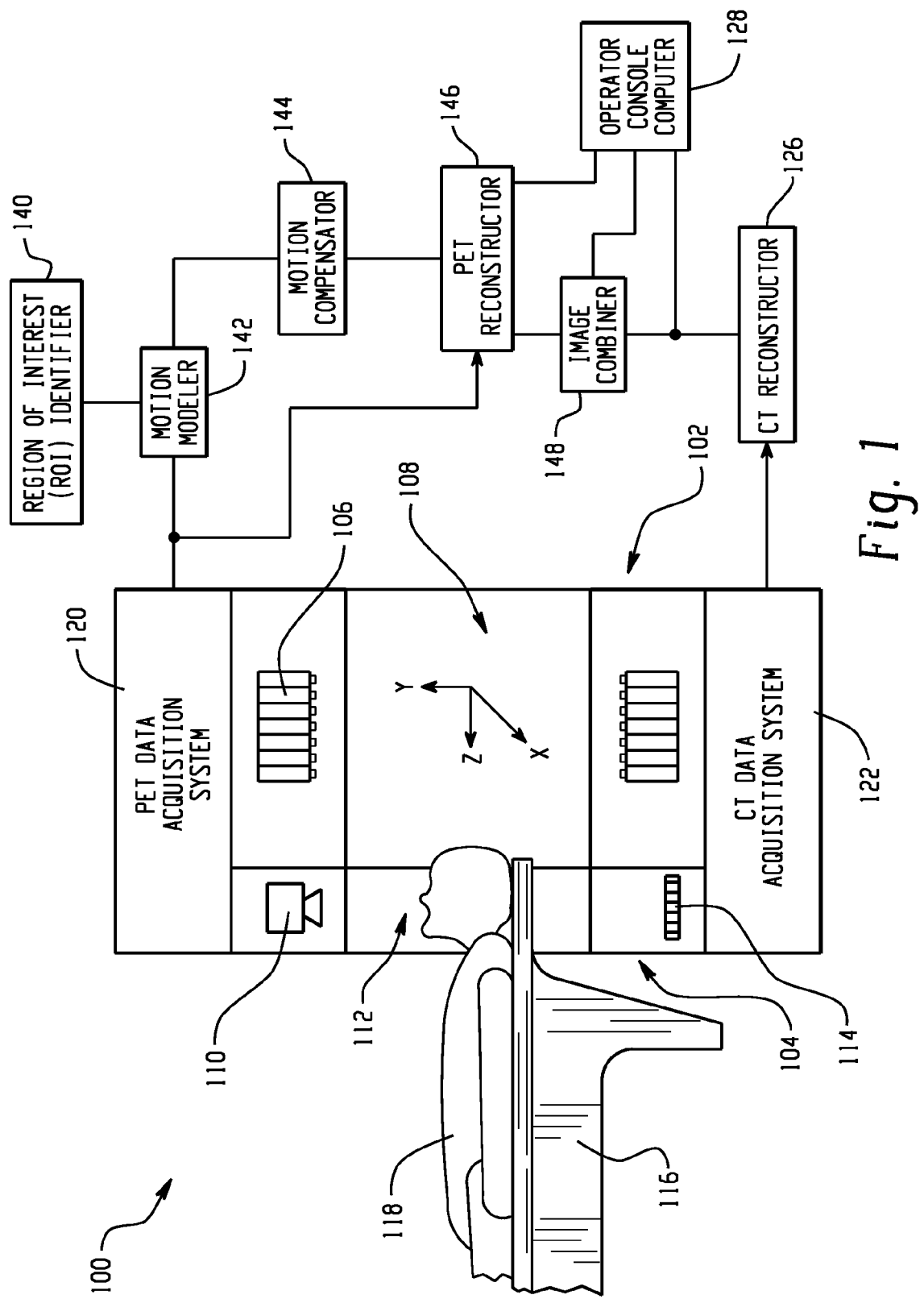

Qi et al., List Mode Reconstruction for PET with Motion Compensation: a Simulation Study, 2002 IEEE International Symposium on Biomedical Imaging, 2002, pp. 413-416.

Visvikis et al., Evaluation of Respiratory Motion Effects in Comparison with Other Parameters Affecting PET Image Quality, 2004 IEEE Nuclear Science Symposium Conference Record, Oct. 2004, pp. 3668-3672, vol. 6.

Qiao et al., A Motion-Incorporated Reconstruction Method for Gated PET Studies, Phys. Med. Biol., 2006, pp. 3769-3786, vol. 51, abstract attached.

Qiao et al., Region of Interest Motion Compensation for PET Image Reconstruction, Physics in Medicine and Biology, 2007, pp. 2675-2689, vol. 52, IOP Publishing Ltd.

Bundschuh et al., Postacquisition Detection of Tumor Motion in the Lung and Upper Abdomen Using List-Mode PET Date: A Feasibility Study, The Journal of Nuclear Medicine, May 2007, pp. 758-763, vol. 48, No. 5.

Brinks, R., et al.; Local Compensation for Respiratory Motion in List-mode PET; 2007; Springer Proceedings in Physics; vol. 114; pp. 31-36.

Klein, G. J., et al.; Fine-scale motion detection using intrinsic list mode PET information; 2001; Mathematical Methods in Biomedical Image Analysis; pp. 71-78.

* cited by examiner

MOTION CORRECTION IN NUCLEAR IMAGING

CROSS REFERENCE TO RELATED APPLICATIONS

This application claims the benefit of U.S. provisional application Ser. No. 60/951,968 filed Jul. 26, 2007, which is incorporated herein by reference.

The following relates to motion compensation in imaging, and especially to motion compensation in nuclear imaging modalities such as positron emission tomography (PET) and single photon emission computed tomography (SPECT), and the like. It finds particular application to medical and other applications where it is desirable to correct for motion in an object under examination.

Positron emission tomography (PET) is a branch of nuclear medicine in which a positron-emitting radiopharmaceutical such as $^{18}$F-fluorodeoxyglucose (FDG) is introduced into the body of a patient. As the radiopharmaceutical decays, positrons are generated. More specifically, each of a plurality of positrons reacts with an electron in what is known as a positron annihilation event, thereby generating a coincident pair of 511 keV gamma rays which travel in opposite directions along a line of response (LOR). A gamma ray pair detected within a coincidence time is ordinarily recorded by the PET scanner as an annihilation event. In a time of flight (TOF) PET scanner, the difference in the arrival times of the coincident gamma ray pairs is also measured. The TOF information is used to predict the most likely position of the annihilation along the LOR. The many events acquired during a scan are reconstructed to produce image or other data indicative of the distribution of the radionuclide in the patient.

One factor that can influence the quality of the image data is object motion. A human patient, for example, will ordinarily undergo physiological motion such as cardiac and respiratory motion during the course of a scan. Unless accounted for, the object motion can introduce blurring and other artifacts in the reconstructed image data.

One technique for accounting for such motion has been the use of gating. In cardiac imaging, a physiological monitor such an electrocardiogram (ECG) has been used. In a prospective gating technique, projection data is acquired only at a desired cardiac phase or phases. In a retrospective gating technique, projection data is selected and reconstructed depending on the cardiac phase at which it was acquired. Similar gating techniques have been used in connection with respiratory motion.

One disadvantage of gating techniques is the motion of the object may be aperiodic or otherwise vary from one motion cycle to the next. Another is that only a subset of the potentially available projection data is used to reconstruct the image. Unfortunately, the decreased count statistics tend to increase image noise, thus negating the image quality improvement provided by the reduced blurring. In the case of lung imaging, it has been suggested that a minimum of some six to eight million counts per gate are required to observe an image quality improvement. See Visvikis, et al., *Evaluation of respiratory motion effects in comparison with other parameters affecting PET image quality*, IEEE Nuclear Science Symposium Conference Record, Vol. 6 pp: 3668-3672 (2004).

Aspects of the present application address these matters and others.

According to a first aspect, an apparatus includes a motion modeler that models, in a first projection of projection data indicative of radionuclide decays in an object, a motion of projection data of the projection. The apparatus also includes a motion compensator that uses the modeled motion to apply a spatial correction to projection data of the projection.

According to another aspect, a method of compensating for a motion of an object includes modeling, in a first projection of projection data indicative of radionuclide decays in the object, a motion of projection data of the first projection. The method also includes using the modeled motion to apply a spatial correction to projection data of the first projection.

According to another aspect, a method includes determining an object motion-induced temporal variation of a spatial characteristic of projection data acquired in an examination of the object and using the determined temporal variation to correct the projection data. The projection data is indicative of radionuclide decays in the object.

Those skilled in the art will appreciate still other aspects of the present invention upon reading and understanding the appended description.

The invention may take form in various components and arrangements of components, and in various steps and arrangements of steps. The drawings are only for purposes of illustrating the preferred embodiments and are not to be construed as limiting the invention.

Figure 2:
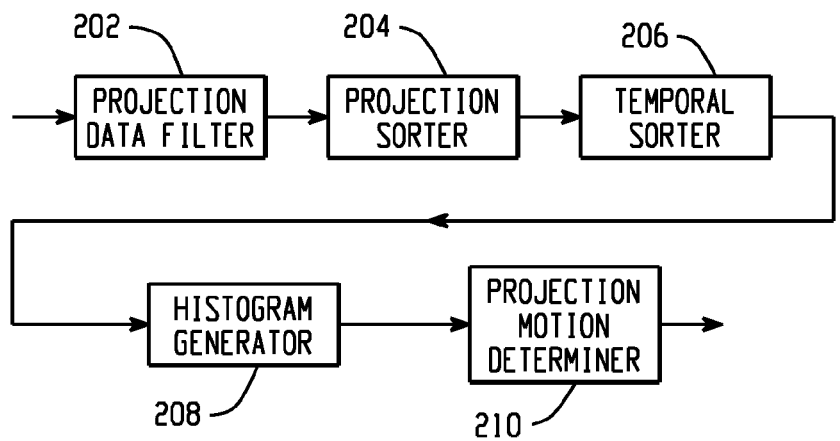
Figure 3:
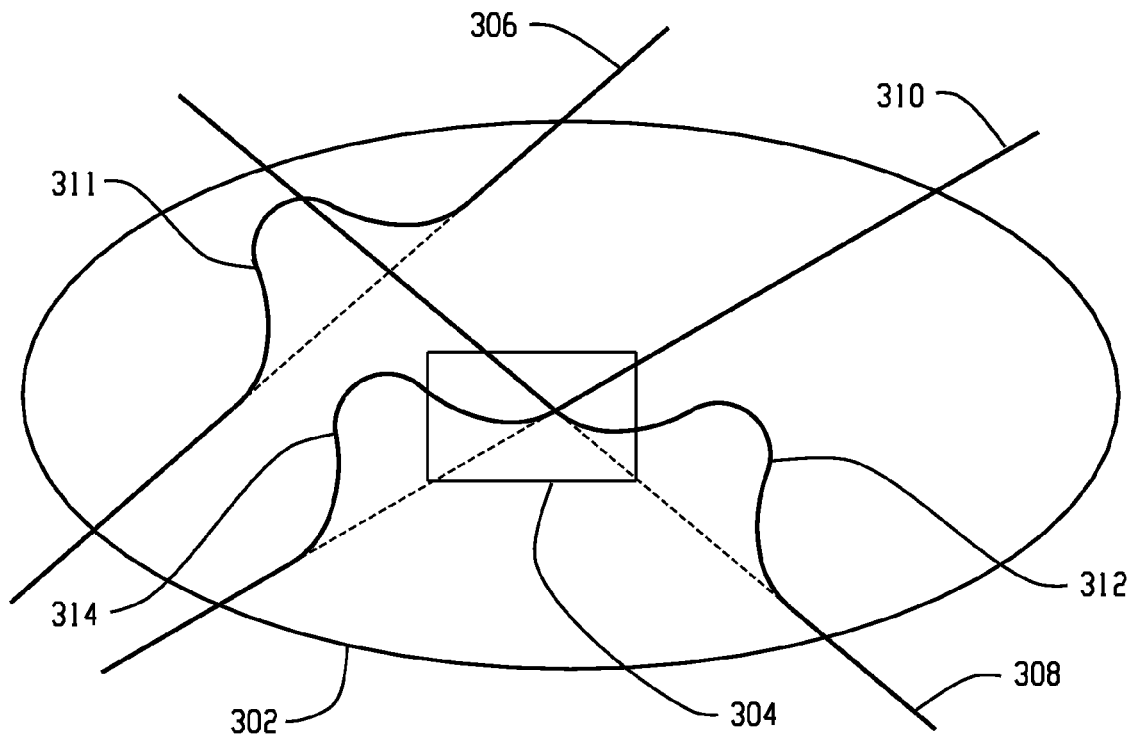
Figure 4:
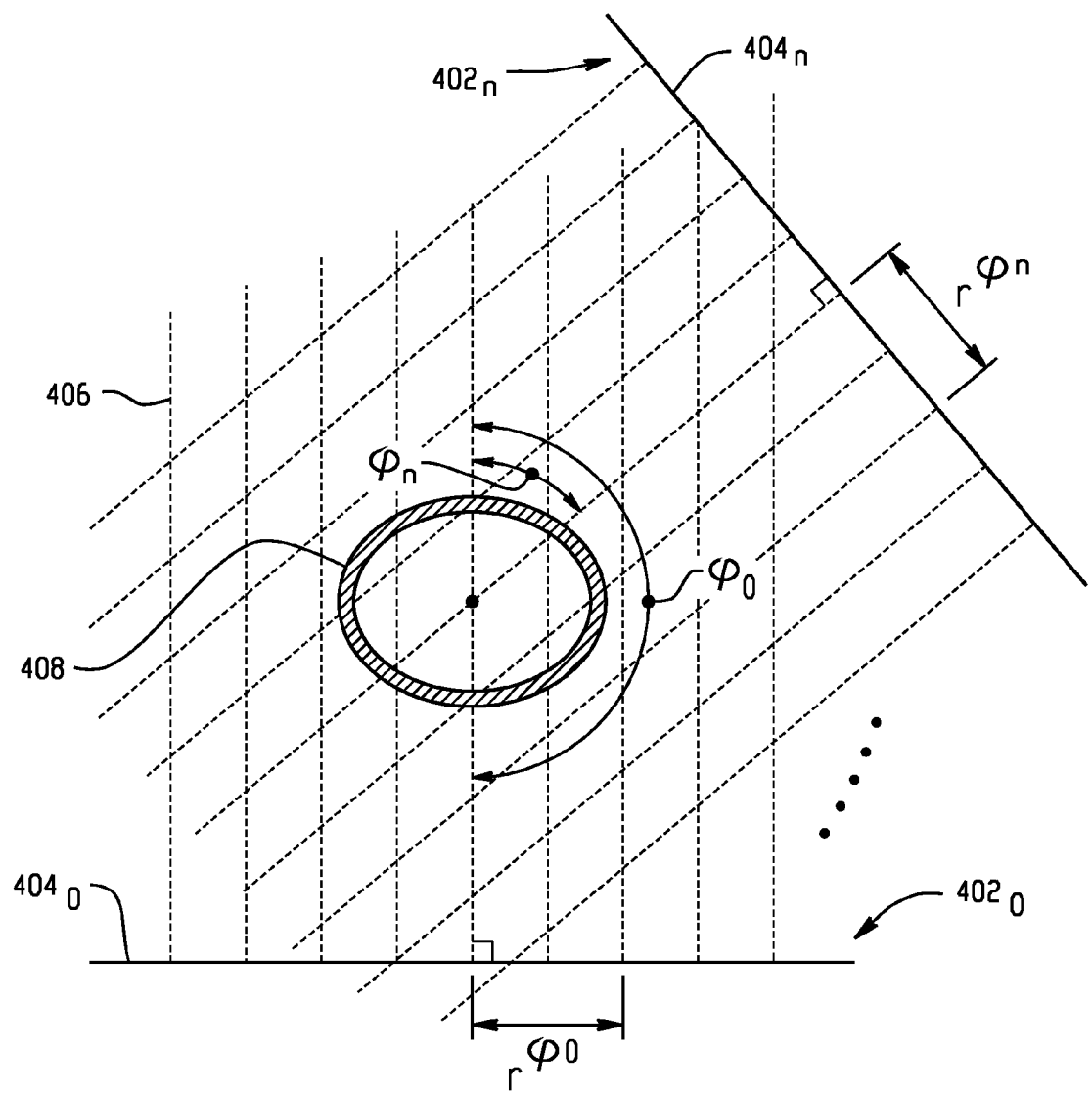
Figure 5:
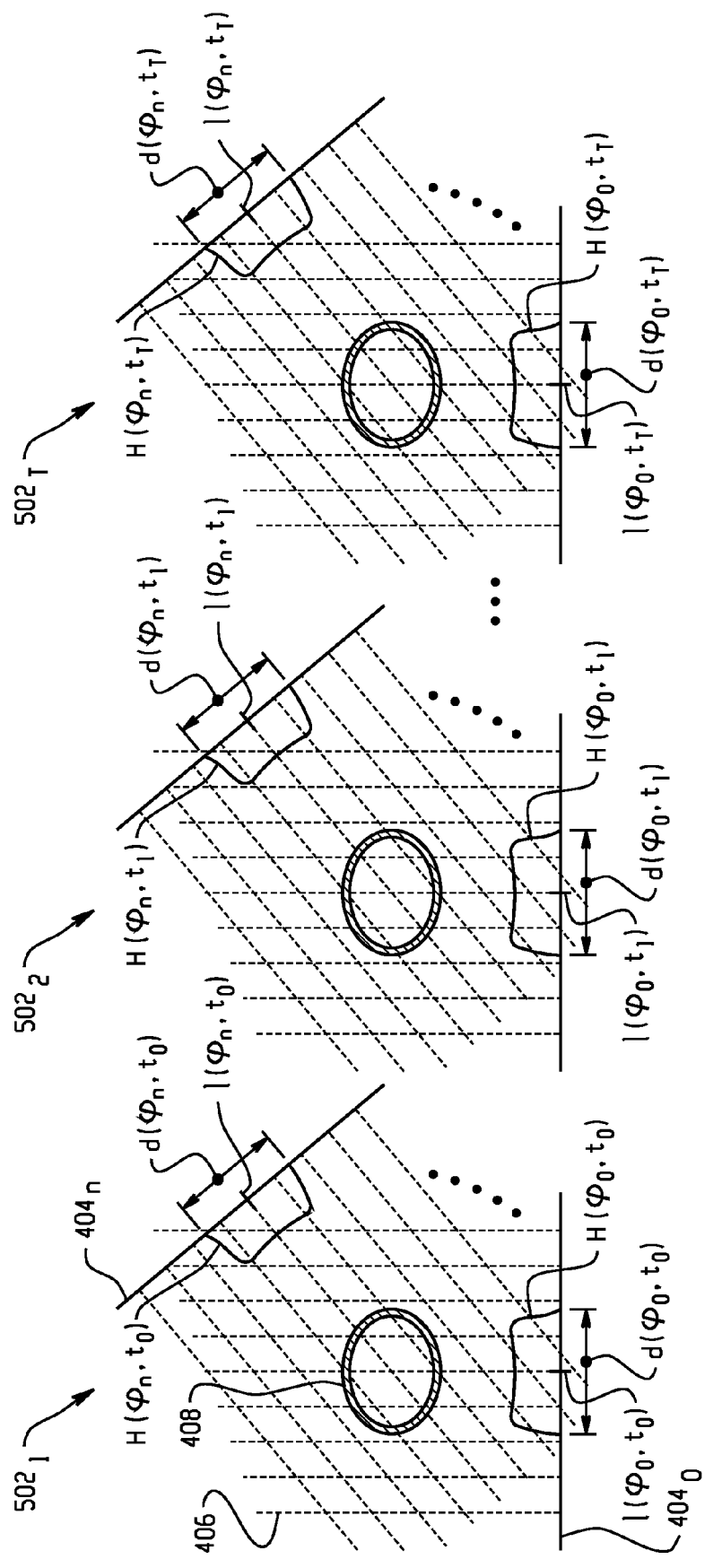
Figure 6A:
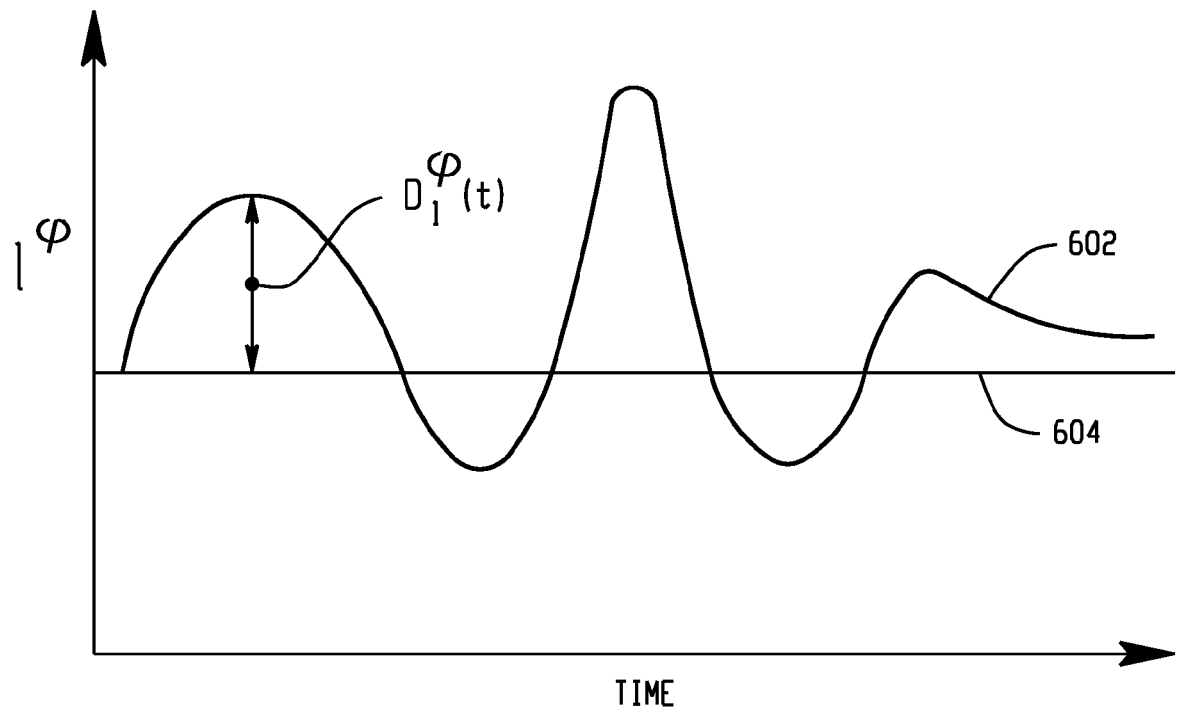
Figure 6B:
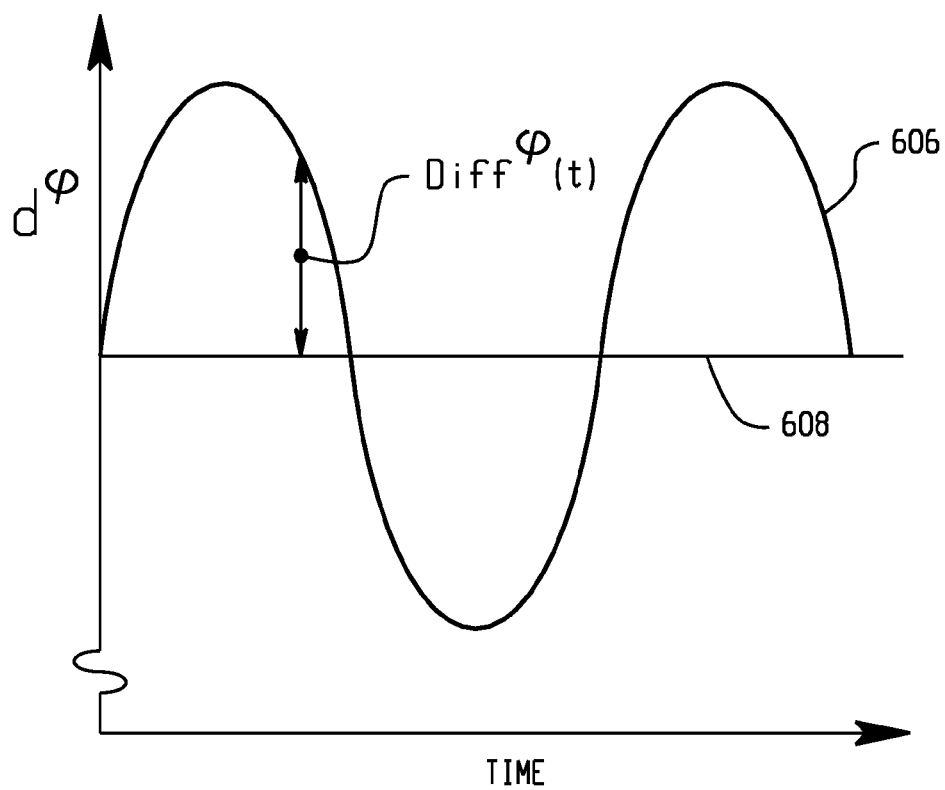
Figure 6C:
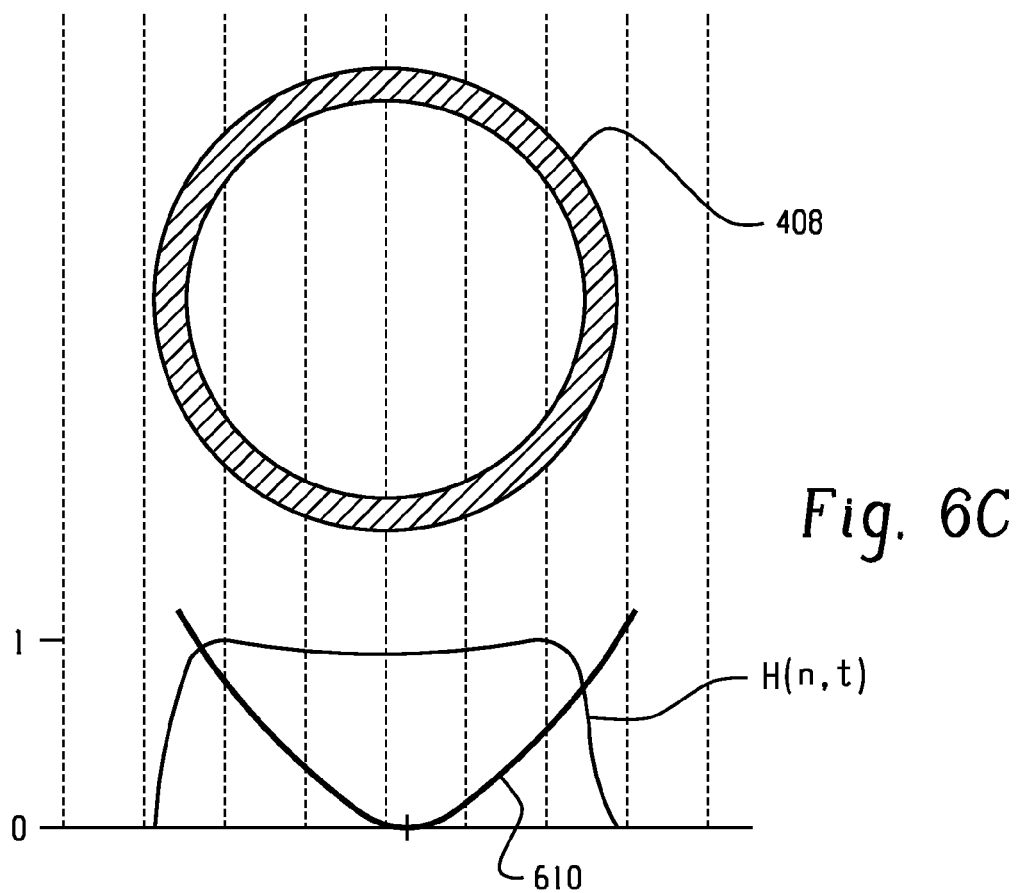
Figure 7:
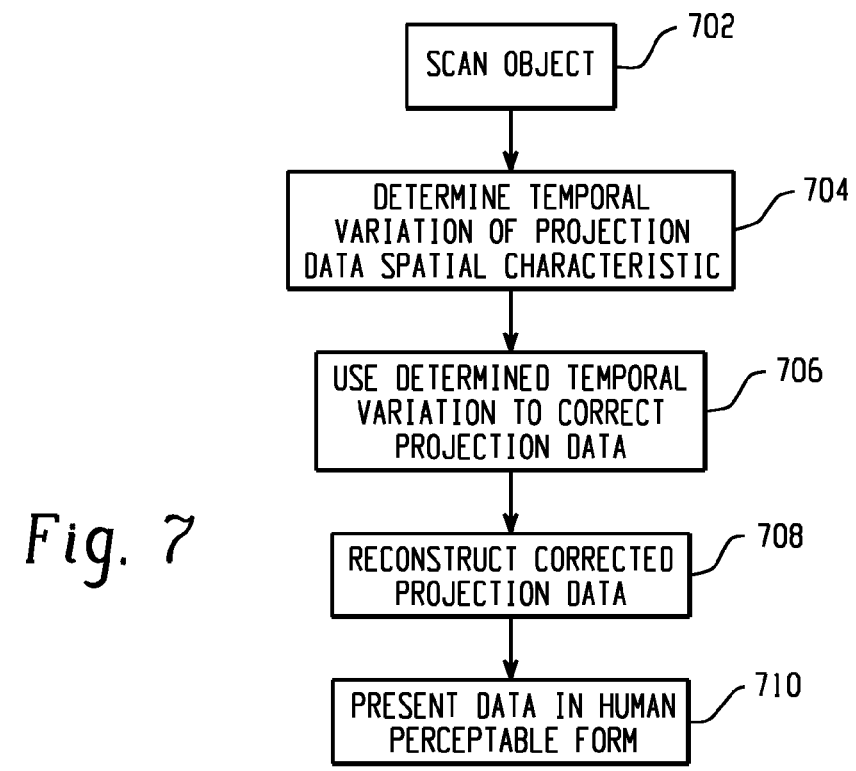

FIG. 1 depicts a combined PET/CT system.
FIG. 2 depicts a motion modeler.
FIG. 3 depicts an operation of a projection data selector.
FIG. 4 depicts an operation of a projection sorter.
FIG. 5 depicts projection- and temporally-sorted projections.
FIG. 6A depicts an operation of a projection data motion determiner.
FIGS. 6B and 6C depict an operation of a projection data motion determiner.
FIG. 7 depicts a method.

With reference to FIG. 1, a combined PET/CT system 100 includes a PET gantry portion 102 and a CT gantry portion 104. The PET gantry portion 102 includes gamma radiation sensitive detectors 106 disposed about an examination region 108 in a generally ring-shaped or annular arrangement. The detectors 106 detect gamma radiation characteristic of positron annihilation events occurring in the PET examination region 108.

The CT portion 104 includes a radiation source 110 such as an x-ray tube that rotates about a CT examination region 112. Radiation sensitive detectors 114 detect radiation emitted by the x-ray source that has traversed the examination region 112.

As illustrated in FIG. 1, the PET gantry portion 102 and CT gantry portion 104 are located in proximity with their respective examination regions 108, 112 disposed along a common longitudinal or z-axis. An object support 116 supports an object to be imaged 118 such as human patient. The object support 116 is longitudinally movable in coordination with operation of the PET/CT system 100 so that the object 118 can be scanned at a plurality of longitudinal locations by both the PET and CT gantry portions 102, 104.

A CT data acquisition system 122 processes the signals from the CT detectors 114 to generate CT projection data indicative of the radiation attenuation along a plurality of lines or rays through the examination region 112. A CT reconstructor 126 reconstructs the CT projection data using suitable reconstruction algorithms to generate image data indicative of the spatially varying radiation attenuation of the object 118.

A PET data acquisition system 120 produces PET projection data such as a list of annihilation events detected by the detectors 106 during an image acquisition. List mode projection data typically includes a list of the detected events, with each entry in the list including information such as a time at which the event was detected, as well as the position and orientation of the corresponding LOR. In the case of a scanner having TOF capabilities, an estimate of the position of the annihilation along the LOR is also provided. Alternately, the acquired data may be sorted or binned into sinogram or projection bins.

A local region of interest (ROI) identifier 140 identifies a volume of interest that includes an organ, lesion, or other feature of the object that is subject to physiological or other motion during the course of the PET data acquisition. In one technique, the ROI is manually delineated by the user using a CT image of the object, a low resolution or non-motion compensated PET image, or the like. In another, the ROI is identified using a priori information about the object. In the case of a human patient, for example, the location of an ROI that includes an organ such as the heart or lungs may be estimated using known morphological characteristics. In still another implementation, a computer processor identifies a location of the ROI either automatically or semi-automatically in a low resolution or other reconstruction of the CT or PET system data. Note that the foregoing techniques may be combined; other suitable techniques may also be used.

As will be described more fully below, the system also includes a motion modeler 142 and a motion compensator 144 that cooperate to compensate for a motion of the object during the PET data acquisition. More specifically, the motion modeler 142 models, in projections of the acquired projection data, a motion of the object. The motion compensator 144 uses the modeled motion to apply a spatial correction to the projection data.

A PET reconstructor 146 uses an iterative or other suitable reconstruction technique to reconstruct the corrected projection data, hence generating motion corrected image space data indicative of the distribution of the radionuclide in the object 118. Data from the CT portions may be used to provide suitable attenuation corrections.

The system may also include an image combiner 148 that combines the image data from the CT 126 and PET 146 reconstructors, for example by superimposing or otherwise combining the combined images for presentation to a user. Use of an image combiner 148 is especially useful where it is desirable to understand the spatial relationship between features visible in the CT and PET image data.

A workstation computer serves an operator console 128. The console 128 includes a human readable output device such as a monitor or display and input devices such as a keyboard and mouse. Software resident on the console 128 allows the operator to perform functions such as interacting with the ROI identifier 140, viewing or otherwise manipulating the image data generated by the PET and CT reconstructors 144, 126, establishing desired scan protocols, initiating and terminating scans, and the like.

It will be understood that variations on the system 100 are also possible. For example, the CT portion of the scanner may be omitted, located remotely from the PET gantry portion 102, or replaced with another imaging device such as a magnetic resonance (MR) scanner. As another example, attenuation or anatomical information may be provided by a transmission source associated with the PET gantry portion 102.

Turning now to FIG. 2, the motion modeler 142 includes a projection data filter 202, a projection sorter 204, a temporal sorter 206, a histogram generator 208, and a projection motion determiner 210.

The projection data filter 202 filters the acquired projection data so as to disregard those events resulting from radionuclide decays occurring outside the identified ROI (or, stated conversely, to select those events indicative of radionuclide decays occurring in the ROI).

Various filtering techniques are contemplated. For example, the filter may, but need not, select or disregard the events on a binary basis. In the latter case, the filter 202 may assign a relative weight to an event as a linear or other function of the probability that the event occurred in the ROI. In the former case, the probability that an event occurred within the ROI can be compared to a threshold value, and the event selected or disregarded accordingly.

FIG. 3 depicts an operation of the projection data filter 202 in relation to an object 302 and an ROI 304. For the purposes of the present example, the projection data is assumed to be TOF PET projection data that includes example first 306, second 308, and third 310 events. The positions of the events along the LORs are indicated by respective probability functions 311, 312, 314.

As illustrated, the LORs of the second 308 and third 310 events intersect the ROI 304, while the LOR of the first event 306 does not. Also as illustrated, the second event 308 is relatively less likely to have originated in the ROI 306 than the third 310.

Thus, according to one filtering technique, the first event 306 would receive a weight of zero, the second event 308 would receive an intermediate weight, and third event 310 would receive a relatively higher weight. According to another technique, the first event 306 would be disregarded as its LOR does not intersect the ROI 306. The second 308 and third 310 would be compared against the threshold and selected or disregarded accordingly (or stated another way, assigned a weight of one or zero, as the case may be).

Returning to FIG. 2, the motion modeler 142 also includes a projection sorter or binner 204 sorts the filtered events into to a plurality N of projection bins or groups according to their transverse and/or axial projection angles. Each projection group typically includes a range of projection angles, with the number and location of groups and the range of angles in each group depending on factors such as the scanner geometry, the acquisition statistics, the desired angular resolution of the motion compensation, and the like. Note that the various groups may have unequal angular ranges and may otherwise be located at unequal angular intervals. Where the objective is to compensate the motion of the object in three dimensions, the location of the various projections is selected accordingly, again subject to the acquisition geometry of the scanner.

Two of the N projections $402_0$, $402_n$ are shown in FIG. 4 for an example case of an ROI that includes a feature of interest 408. The first example projection $402_0$, is characterized by a projection angle $\phi_0$ and a projection surface $404_0$ (e.g., a plane, curved plane, or a line); the second example projection $402_n$ is characterized by a projection angle $\phi_n$ and a projection surface $404_n$. Hence, those events located having a projection angle of about $\phi_0$, are sorted or binned in the first projection group $402_0$, while those events having a projection angle of about $\phi_n$ are sorted or binned in the second projection group $402_0$. The position of the each event can be described by the location $r^{\phi 0}$, $r^{\phi n}$ at which its LOR 406 intersects the projection plane $404_0$, $404_n$.

Returning now to FIG. 2, the temporal sorter or binner 206 sorts the events of the various projections 404 into a plurality T of temporal bins or groups. Again, the number of temporal groups and the temporal width of each group depends on factors such as the acquisition statistics, the desired temporal resolution of the motion compensation, the number N of projection groups, and the like. Examples of various projection- and temporally-sorted groups following the projection and temporal sorting operations are illustrated in FIG. 5 for example time periods $502_1, 502_2 \ldots 502_T$.

Returning now to FIG. 2, the histogram generator 208 generates projection data histograms H(n, t) for each of the temporal groups of each projection. The histograms represent the projection of the activity in the ROI 304 on to the respective projection planes 404. In one example, the histograms are generated by counting or summing those events having similar coordinates r in their respective projection planes. In another, the events are weighted according to the weights produced in connection with the LOR filtering process described above. Example histograms $H(\phi_n, T_t)$ generated for the various projections and temporal groups are illustrated schematically in FIG. 5.

Note that the sequence of the projection data filtering, sorting and histogram generation operations may be varied from that described above. Thus, for example, the temporal sorting may be performed prior to the projection sorting. As another example, the selection, sorting, and/or histogram generation operations may be performed on an event-by-event basis. One or more spatial or temporal filters may also be used to apply desired smoothing, sharpening, band pass, or other desired filter functions. The filters may be applied to the projection data prior to generating the histograms, to the already generated histograms, or both.

Returning again to FIG. 2, a projection motion determiner 210 uses the histogram data to determine a motion of the projection data in each of the projections. With additional reference to FIG. 5, the histograms H(n,t) may be characterized by time-varying spatial features such as locations $1(n,t)$ and/or dimensions d(n,t). Examples of location information include geometric centers and centers of activity; examples of dimension information include the distance between the outer edges of the feature of interest 408, or the histogram itself.

By way of an example in which the feature 408 includes the myocardium, the location of the heart and hence locations of the histograms with respect to their respective projection planes 404 may vary as a function of the subject's respiratory motion, while the size of the heart and hence the dimensions of the histograms can ordinarily be expected to vary with the expansion and contraction of the beating heart.

An operation of the projection motion determiner 210 in the case of a time varying histogram location 1 will now be described with reference to FIG. 6A. For each projection, the histogram data for each time bin is used to determine the location as a function of time, which function $1^\Phi(t)$ is illustrated for an example projection by the curve 602. A reference location 604 is selected, and the difference between the actual and reference locations provides a time varying displacement vector $D_1^\Phi(t)$ that describes the displacement of the histogram, and hence the myocardium, in the projection plane 404.

For an object having a time-varying dimension d (e.g., the diameter of the myocardium), the magnitude of the motion of the events as projected into the respective histograms ordinarily vary as a function of their position relative to the object and hence their location in the projection plane 404. An operation of the projection motion determiner 210 in such a case will now be described with reference to FIGS. 6B and 6C. For each projection, the histogram data from each time bin is used to determine the dimension as a function of time, which function $d^\Phi(t)$ is illustrated by the curve 606 of FIG. 6B. The average value of the dimension is also determined, which function $d^\Phi(avg)$ is illustrated by line 608.

For each projection, the time-varying difference $\text{Diff}^\Phi(t)$ between the actual and average dimensions is calculated for the various temporal groups. Turning now to FIG. 6C, the difference $\text{Diff}^\Phi(t)$ is weighted by a weighting function 610 that compensates for a spatially varying displacement of the feature 406 and hence the LORs in the projection. As shown in FIG. 6C, the weighting function 610 has a value of zero at the center of motion and one at the outer boundary of the feature of interest 406. Note that the center of motion may be approximated as the geometric center of the object. The weighting is carried out over the time period of the image acquisition or other desired time period so as to generate a spatially and temporally varying displacement vector $D_2^\Phi(r, t)$.

The motion compensator 144 applies the displacement vector or vectors $D_1^\Phi(t)$, $D_2^\Phi(r,t)$ to those events selected by the projection filter 202, hence generating motion corrected data set. The motion corrected data set is reconstructed as desired.

Operation will now be further described with reference to FIG. 7.

The object is scanned at 702. During the scan, portions of the object may undergo periodic or other motion. Upon completion of the scan, the presence of the object is no longer required.

A temporal variation of one or more spatial characteristics of the projection data acquired during the scan is determined at 704. As noted above, for example, the spatial characteristics may include one or both of a location or a dimension of the data in one or more projections.

At 706, the determined temporal variation is used to correct the projection data. As noted above, for example, one or more temporally and/or spatially varying displacement vectors may be generated and applied to the projection data.

At 708, the corrected projection data is reconstructed so as to produce image space data.

At 710, information indicative of the reconstructed image space data is presented in human readable form, for example by displaying an image representative of the radionuclide distribution of the object.

Those of ordinary skill in the art will recognize that the various techniques described above, and especially those of the ROI identifier 140, motion modeler 142, motion compensator 144, image combiner 148, and reconstructors 146, 148 may be implemented by way of computer readable instructions stored on a computer readable storage medium accessible to a computer processor. When executed, the instructions cause the processor(s) to carry out the described techniques. Note that the medium need not be local to the processor; the instructions may be downloaded or otherwise accessed via a communication network such as the internet. The relevant computers may also be located remote from the imaging system, with the scan data transferred via a suitable network or other medium.

Variations and alterations are contemplated. For example, the above-described techniques are not limited to use in cardiac imaging and may be used in connection with other organs, tumors or other lesions, and/or features of a human patient or other animate or inanimate object. Moreover, the techniques may used to compensate for motion other than cardiac and respiratory motion. The techniques are also not limited to use with TOF PET and may also be used in connection with non-TOF PET data, multi-pinhole SPECT, and other modalities. Where time of flight or other analogous information is not available, the projection data selector 202 would ordinarily select those projections that intersect the region of interest. The projection data selector 202 may also be omitted, particularly where the activity is concentrated in a portion of the object or where the motion of the various portions of the object is relatively uniform.

In still another variation, the techniques may be applied to sinogram-based image acquisitions. According to such an example, the acquired projection data should ordinarily be stored in desired temporal bins or frames at the time of the acquisition. According to such an example, one or both of the projection 402 and temporal 404 binners may be omitted.

The motion correction may be applied in only a single projection or otherwise in limited number and/or range of projections. Such an implementation is especially useful where the motion of the object is confined or otherwise limited to a single or a small number of directions. Where the object motion is uniform across the various projections, the projection binner 402 may also be omitted.

The invention has been described with reference to the preferred embodiments. Of course, modifications and alterations will occur to others upon reading and understanding the preceding description. It is intended that the invention be construed as including all such modifications and alterations insofar as they come within the scope of the appended claims.

What is claimed is:

1. An apparatus comprising:
   a projection data filter that filters projection data indicative of radionuclide decays in an object to select events indicative of radionuclide decays occurring in a sub-region of the object;
   a motion modeler that models, in a first projection of the filtered projection data, a motion of the object;
   a motion compensator that uses the modeled motion to apply a spatial correction to projection data of the projection.

2. The apparatus of claim 1 wherein the motion modeler models, in a plurality of projections of projection data indicative of radionuclide decays in the object, a motion of the object.

3. The apparatus of claim 1 wherein the motion modeler models a time-varying spatial characteristic of projection data of the projection.

4. The apparatus of claim 3 wherein the characteristic includes the location of a center of the projection data.

5. The apparatus of claim 1 wherein the motion modeler generates a time-varying spatial displacement vector and the motion compensator uses the displacement vector to compensate for a motion of the object.

6. The apparatus of claim 1 wherein the motion modeler uses a spatially varying weighting function to compensate for a spatially varying displacement of a feature of the object.

7. The apparatus of claim 6 wherein the motion modeler determines a difference between a first spatial dimension of the projection data of the projection and a second spatial dimension of the projection data and applies the weighting function to the determined difference.

8. The apparatus of claim 1 wherein the projection data filter weights an event according to one of at least three different weight values as a function of the likelihood that the event is indicative of a radionuclide decay occurring in the sub-region.

9. The apparatus of claim 1 including a projection sorter and a temporal sorter that sort the projection data into a plurality of projections and temporal groups.

10. The apparatus of claim 1 including a histogram generator that generates a histogram of projection data of the projection.

11. The apparatus of claim 10 wherein the projection data of the projection includes projection data indicative of radionuclide decays occurring at a first and second times during an examination of the object and the histogram generator generates a first histogram of projection data indicative of radionuclide decays occurring at the first time and a second histogram of projection data indicative of radionuclide decays occurring at the second time.

12. The apparatus of claim 10 including a projection motion determiner that uses the histogram to determine a motion of the object.

13. The apparatus of claim 1 wherein apparatus forms part of a positron emission tomography detector.

14. A method of compensating for a motion of an object, the method comprising:
   modeling, in a first projection of projection data indicative of radionuclide decays in the object, a motion of the object;
   using the modeled motion to apply a spatial correction to projection data of the first projection;
   using projection data of the first projection to model a first distribution of a radionuclide in the object at a first time during an examination of the object; and
   using projection data of the first projection to model a second distribution of a radionuclide in the object at a second time during an examination of the object.

15. The method of claim 14 including:
   modeling a time-varying spatial characteristic of the first and second distributions;
   determining a variation between a value of the modeled time-varying spatial characteristic and a second value;
   using the determined variation to generate a time-varying displacement vector.

16. The method of claim 15 wherein the method includes weighting the determined variation according to a spatially varying weighting function and the step of using the determined variation includes using the weighted determined variation to generate a time- and spatially-varying displacement vector.

17. The method of claim 15 wherein the second value includes an average value of the modeled characteristic.

18. The method of claim 14 wherein the projection data includes projection data indicative of a beating heart and using includes using the modeled motion to compensate for a motion induced by a contraction of the heart.

19. A motion compensation method comprising:
   determining an object motion-induced temporal variation of a spatial characteristic of projection data acquired in an examination of the object, wherein the projection data is indicative of radionuclide decays in the object;
   using the determined temporal variation to correct the projection data;
   using the motion corrected projection data to generate image space data; and
   presenting information indicative of the image space data in human perceptible form.

20. The method of claim 19 wherein the spatial characteristic includes at least one of a location or a dimension of a projection of the projection data on a projection surface.

21. The method of claim 20 wherein spatial characteristic includes a dimension and the method includes compensating for a spatially non-uniform temporal variation the dimension of the projection of the data on the surface.

22. The method of claim 19 wherein determining includes determining the temporal variation of the spatial characteristic in each of a plurality of projections of the projection data and using includes the determined variations to correct the projection data of the projections.

23. The method of claim 19 wherein the projection data includes list mode time of flight positron emission data and the method includes:

filtering the projection data to select projection data indicative of positron annihilations occurring in a sub-region of the object;

sorting the projection data into a plurality of projections and temporal groups;

for each of a plurality of projections and temporal groups, generating a histogram indicative of a spatial distribution of positron emissions in the object;

using the histograms to model a motion of the object.

24. The method of claim 23 wherein using the histograms includes using the histograms to model a motion of the object in three spatial dimensions.

* * * * *